ual Patent [19] [11] 3,962,219
Dorlars et al. [45] June 8, 1976

[54] OPTICAL BRIGHTENERS
[75] Inventors: Alfons Dorlars, Leverkusen; Otto Neuner, Bergisch,Gladbach; Hans Theidel, Leverkusen, all of Germany
[73] Assignee: Bayer Aktiengesellschaft, Leverkusen, Germany
[22] Filed: Sept. 27, 1974
[21] Appl. No.: 509,839

[30] Foreign Application Priority Data
Oct. 2, 1973   Germany............................ 2349480

[52] U.S. Cl. ...................... 260/240 D; 260/240.9; 252/301.24
[51] Int. Cl.² ............... C07D 417/02; C07D 277/64
[58] Field of Search...................... 260/240 D, 240.9

[56] References Cited
UNITED STATES PATENTS
3,427,307   2/1969   Schinzel et al.................. 260/240 D
3,597,364   8/1971   Okubo et al. ................... 260/240 D
3,674,781   7/1972   Schinzel et al.................. 260/240 D
FOREIGN PATENTS OR APPLICATIONS
967,483   9/1962   United Kingdom OTHER PUBLICATIONS
Postovskii, Chem. Abstracts, 58(1963), col. 9049–9050.
Beilstein, vol. 27EII, (1955), p. 883.

Primary Examiner—Arthur P. Demers
Attorney, Agent, or Firm—Plumley & Tyner

[57] ABSTRACT
Compounds of the formula

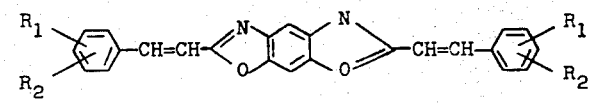

wherein $R_1$ and $R_2$ denote hydrogen, halogen, nitrile, alkoxy, alkyl, aryl, cycloalkyl, aralkyl, carboxyl or carboxylic acid ester groups are suitable for the optical brightening of synthetic organic high molecular materials.

5 Claims, No Drawings

OPTICAL BRIGHTENERS

The present invention relates to compounds of the formula

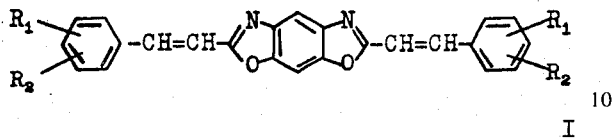

I and to their preparation and use as brighteners.

In the general formula I $R_1$ and $R_2$ independently of one another denote hydrogen, halogen or nitrile, alkoxy, alkyl, aryl, cycloalkyl, aralkyl, carboxyl or carboxylic acid ester groups.

The said radicals can carry further substituents, customary in brightener chemistry.

Suitable alkyl and alkoxy radicals are radicals with 1–6 C atoms which can be substituted further, for example by OH, $C_1$–$C_4$-alkylcarbonyloxy or halogen (F, Cl and Br).

Suitable cycloalkyl radicals are those with 5–7 ring members which can be substituted, for example by $C_1$–$C_4$-alkyl.

Suitable aryl radicals are phenyl radicals; suitable aralkyl radicals are phenyl-$C_1$–$C_4$-alkyl radicals and in both cases the phenyl radicals can have 1 to 3 $C_1$–$C_4$-alkyl substituents.

Suitable carboxylic acid ester groups are $C_1$–$C_4$-alkoxycarbonyl groups which can be substituted, preferably monosubstituted, by OH, halogen (F, Cl or Br), OH or $C_1$–$C_4$-alkoxy.

The following may be mentioned, inter alia, as examples of the radicals $R_1$ and $R_2$: hydrogen, methyl, ethyl, propyl, isopropyl, butyl, sec.- and tert.-butyl, cyclohexyl, benzyl, phenyl, tolyl, chlorophenyl, fluorine, chlorine, bromine, nitrile, methoxy, ethoxy, propoxy, butyroxy, benzyloxy, β-methoxyethoxy, β-chloroethoxy, β-hydroxyethoxy, carboxyl, methoxycarbonyl, ethoxycarbonyl and β-methoxyethoxycarbonyl.

So-called "bulky" radicals, such as, for example, tert.-butyl, are preferably in the m- or p-position. Particularly valuable brighteners are those of the formula I, wherein $R_1$ is hydrogen, $C_1$–$C_4$-alkyl, $C_1$–$C_4$-alkoxy, $C_1$–$C_2$-alkoxy-$C_1$–$C_4$-alkoxy, chlorine, nitrile, phenyl, COOH or $C_1$–$C_4$-alkoxycarbonyl and $R_2$ is hydrogen, $C_1$–$C_4$-alkyl or chlorine.

Very particularly valuable compounds are those in which $R_1$ represents m-located $C_1$–$C_4$-alkyl, chlorine, $C_1$–$C_4$-alkoxy or hydrogen and $R_2$ denotes hydrogen.

The new distyryl-benzobisoxazoles of the formula I can be prepared in various ways.

For example, cinnamic acids of the formula II

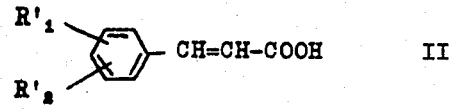

II in which $R'_1$ and $R'_2$ represent hydrogen, halogen, nitrile, alkyl, alkoxy, cycloalkyl, aralkyl or aryl can be condensed with a half-molar amount of diaminoresorcinol of the formula III

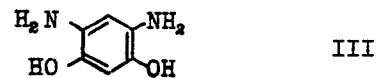

III in a manner which is in itself known (compare, for example, Venkataraman, The chemistry of synthetic dyes, volume 5 (1971, page 621 et seq.) to give the desired benzobisoxazoles I, suitably at an elevated temperature, for example in polyphosphoric acid or pyrophosphoric acid, or in the presence of boric acid. This reaction can also be carried out in two stages, by, for example, converting diaminoresorcinol III, with the aid of the cinnamoyl chlorides corresponding to the cinnamic acids II, into the bis-cinnamoylamino-resorcinol derivatives IV

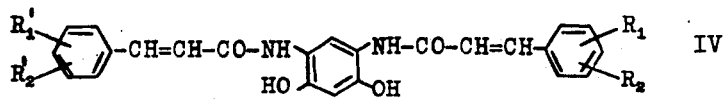

IV and then cyclising these, in polyphosphoric acid or pyrophosphoric acid or in the presence of boric acid, to the bisoxazoles I, in a manner which is in itself known (compare, for example, Venkataraman, l.c., page 624 et seq.).

The compounds of the formula II are known (compare, for example, Organic Reaktions, volume 1, page 256–263). As examples there may be mentioned cinnamic acid; o-, m- and p-chlorocinnamic acid; o-, m- and p-methylcinnamic acid and m- and p-ethylcinnamic acid; m- and p-propylcinnamic acid and m- and p-butylcinnamic acid; 2,5-dimethylcinnamic acid; o-, m- and p-methoxycinnamic acid and ethoxycinnamic acid; m- and p-cyanocinnamic acid.

A further possible way of preparing I is the reaction of bis-cinnamoylamino-dihalogenobenzenes of the formula V

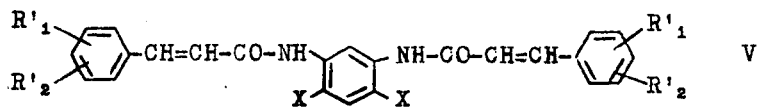

V in which $R'_1$ and $R'_2$ have the indicated meaning and

X represents chlorine or bromine
by heating in an inert medium in the presence or absence of inorganic or organic bases as acid-binding agents, optionally also with addition of copper or copper salts. Such cyclisation reactions are in themselves known and are described, for example in Venkataraman, l.c., page 626.

In cases in which substituted cinnamic acids II are more difficult to obtain, it can be advisable to use the condensation of the suitably substituted benzaldehyde derivatives VI

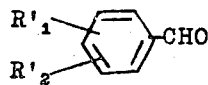

VI

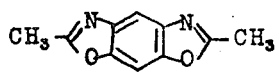

VII in which

R'$_1$ and R'$_2$ have the indicated meaning with a half-molar amount of 2,6-dimethyl-benzo[1,2-d; 5,4-d']-bis-oxazole VII, which is carried out in a manner which is in itself known (compare Venkataraman, l.c., page 634) at elevated temperature in an inert medium, suitably with acid catalysis and with removal of the resulting water of reaction, for example by azeotropic distillation.

Suitable compounds of the formula VI are: benzaldehyde; o-, m- and p-chlorobenzaldehyde; o-, m- and p-tolualdehyde; m- and p-ethylbenzaldehyde; m- and p-propylbenzaldehyde and isopropylbenzaldehyde; m- and p-butylbenzaldehyde, sec.-butylbenzaldehyde and tert.-butylbenzaldehyde; 2,5-dimethylbenzaldehyde; 2-chloro-4-methylbenzaldehyde; p-phenylbenzaldehyde; o-, m- and p-methoxybenzaldehyde; m- and p-ethoxybenzaldehyde and p-propoxybenzaldehyde; m- and p-methoxyethoxybenzaldehyde, m- and p-cyanobenzaldehyde; m- and p-benzaldehydecarboxylic acid.

The compound of the formula VII is known (compare, for example, Ukrain. Chem. Journ. 35, 943 (1969) = C.A. 72/45004 g).

Those distyryl-benzobisoxazole derivatives in which R$_1$/R$_2$ represents the carboxylic acid group or a carboxylic acid alkyl ester group are suitably prepared by saponification of the nitrile compounds in question by means of acids or esterification of the resulting carboxylic acids with alcohols, for example methanol, ethanol, propanol and glycol monomethyl ether (compare, for example, Houben-Weyl, volume 8, page 516 et seq.).

Because of their strong blue fluorescence and their affinity, the distyrylbenzobisoxazoles according to the invention are suitable for brightening various synthetic organic high molecular materials, such as polyolefines (polyethylene and polypropylene), polyvinyl chloride and especially polyesters, for example terephthalic acid polyglycol esters, which can be treated in the form of filaments, woven fabrics, knitted fabrics, films or plastic compositions.

The new brighteners I can be used in the customary manner, in the form of organic solutions or dispersions, by themselves or together with other additives such as dispersing agents, plasticisers, stabilisers or shading dyestuffs. Thus, for example, polyester fabrics can be brightened effectively by padding with aqueous dispersions of the brighteners I and subsequent thermofixing. However, the new bisoxazoles concerned prove to be particularly advantageous when used by the pad-thermosol process, if they are dissolved or suspended in chlorinated hydrocarbons, such as are recently being used in solvent dyeing processes, for example trichloroethylene and perchloroethylene.

EXAMPLE 1a 18.8 g of 2,6-dimethyl-benzo-bis[1,2-d; 5,4-d']oxazole, 23.5 g of benzaldehyde, 40 g of p-toluenesulphonic acid and 20 g of dimethylformamide are stirred into 300 ml of xylene. The mixture is gradually heated to the boil and is stirred at the boil (about 4 hours) until no further water, which is collected in a circulatory water separator, separates off. The resulting distyrylbenzobisoxazole, which separates out as crystals in part already during the reaction, is isolated as a crude product by stripping off the xylene in steam and filtering the aqueous suspension. It is purified by washing with methanol and recrystallisation from boiling chlorobenzene with the addition of fuller's earth, and 24.5 g of greenish-tinged yellow crystals are thus obtained; their solution in dimethylformamide and in chlorobenzene shows an intense, somewhat reddish-tinged blue fluorescence in UV light.

If instead of benzaldehyde, the substituted benzaldehydes listed in the table which follows are used, and in other respects the procedure indicated is followed, the benzobisoxazole derivatives described under 1b to 1v are obtained. The dicarboxylic acids 1w and x can be obtained by saponification of the particular nitriles 1u and v, respectively, with 72% strength sulphuric acid, and the esters 1y and z can be obtained by esterification of the carboxylic acids mentioned with ethanol and glycol monomethyl ether, respectively.

| Example 1 | R$_1$ | R$_2$ | Aldehyde used | Colour of fluorescence in dimethylformamide |
|---|---|---|---|---|
| a | H | H | Benzaldehyde | somewhat reddis-tinged blue |
| b | 2-CH$_3$ | H | o-Tolualdehyde | somewhat reddish-tinged blue |
| c | 3-CH$_3$ | H | m-Tolualdehyde | somewhat reddish-tinged blue |
| d | 4-CH$_3$ | H | p-Tolualdehyde | blue |
| e | 3-C$_2$H$_5$ | H | m-Ethylbenzaldehyde | somewhat reddish-tinged blue |
| f | 4-C$_2$H$_5$ | H | p-Ethylbenzaldehyde | blue |
| g | 4-i-C$_3$H$_7$ | H | p-Isopropylbenzaldehyde | blue |
| h | 4-tert.-C$_4$H$_9$ | H | p-tert.-butylbenzaldehyde | blue |
| i | 2-CH$_3$ | 5-CH$_3$ | 2,5-Dimethylbenzaldehyde | somewhat reddish-tined blue |

-continued

| Example 1 | $R_1$ | $R_2$ | Aldehyde used | Colour of fluorescence in dimethylformamide |
|---|---|---|---|---|
| k | 4- | H | p-Phenylbenzaldehyde | blue |
| l | 2-Cl | H | o-Chlorobenzaldehyde | somewhat reddish-tinged blue |
| m | 3-Cl | H | m-Chlorobenzaldehyde | somewhat reddish-tinged blue |
| n | 4-Cl | H | p-Chlorobenzaldehyde | blue |
| o | 4-$CH_3$ | 2-Cl | o-Chloro-p-tolualdehyde | blue |
| p | 2-$OCH_3$ | H | o-Methoxybenzaldehyde | blue |
| q | 3-$OCH_3$ | H | m-Methoxybenzaldehyde | somewhat reddish-tinged blue |
| r | 4-$OCH_3$ | H | Anisaldehyde | blue |
| s | 3-$OC_2H_5$ | H | 3-Ethoxybenzaldehyde | somewhat reddish-tinged blue |
| t | 3-O—$C_2H_4OCH_3$ | H | 3-β-Methoxyethoxybenzaldehyde | somewhat reddish-tinged blue |
| u | 3-CN | H | 3-Cyanobenzaldehyde | somewhat reddish-tinged blue |
| v | 4-CN | H | 4-Cyanobenzaldehyde | blue |
| w | 3-COOH | H | Saponification of 1u | blue |
| x | 4-COOH | H | Saponification of 1v | blue |
| y | 3-$COOC_2H_5$ | H | Esterification of 1w with ethanol | somewhat reddish-tinged blue |
| z | 4-$COOC_2H_4OCH_3$ | H | Esterificatio of 1x with glycol monomethyl ether | blue |

EXAMPLE 2

26.6 g of 4,6-dibromo-1,3-phenylenediamine in 250 ml of chlorobenzene and 37 g of cinnamic acid chloride are kept boiling under reflux for 2 hours. The mixture is allowed to cool and the product which has separated out is filtered off and dried. Yield: 44 g of 1,3-bis-cinnamoylamido-4,6-dibromobenzene.

This diamide is stirred, without further purification, with 400 ml of dimethylformamide, 125 ml of pyridine and 38 g of copper acetate for 6 hours at 140°. The mixture is then cooled to 0° whilst stirring and the precipitate which has separated out is filtered off, washed thoroughly with methanol containing ammonia and dried. The crude product thus obtained (15 g) is purified by recrystallisation from o-dichlorobenzene, with the aid of fuller's earth as a clarifying agent. 12.2 g of 2,6-distyryl-benzo-bis-[1,2-d; 5,4-d']-oxazole are obtained, exhibiting a somewhat reddish-tinged blue fluorescence in dimethylformamide solution.

EXAMPLE 3

A fabric of polyester fibres (polyethylene glycol terephthalate) is introduced, in a tumbler autoclave, and using a liquor ratio of 1:40, into a bath which contains, per liter, 1.5 g of sodium oleylsulphonate, 1 g of oxalic acid and 0.05 g of one of the brighteners listed in Example 1a-u. The tumbler autoclave is kept at 125° for 45 minutes, with moderate agitation. After cooling, the fabric is rinsed and dried; it shows a clear and attractive brightening of good fastness to light, washing and chlorite.

EXAMPLE 4

A fabric of polyethylene glycol terephthalate filaments is treated, using a ratio of 1:20, in an aqueous liquor which contains 1 g/l of sodium chlorite and, in dispersed form, 0.05 g/l of one of the brighteners listed in Example 1 under a, c, e, f, m, q, s and t. The bath is brought to 125°C over the course of 45 minutes in a high temperature (HT) apparatus and the textile goods are treated at this temperature for a further 45 minutes. After rinsing and drying, the fabric treated in this way shows a very good, light-fast white effect which is substantially more brilliant than that achieved by the treatment with sodium chlorite alone.

The aqueous brightener dispersion can be prepared as follows:

2 parts of one of the brighteners of the formula I which have been mentioned are mixed with 2 parts of a highly sulphonated castor oil, 8 parts of sodium dioctylphenylpolyglycol ether oxide acetate which contains 40 ethoxy groups per molecule, and 80 parts of water. This mixture is finely ground on a suitable pearl mill, until about half of all the particles are of size 0.5–1µ and is then diluted with water to a concentration of approx. 10%, relative to the brightener, and homogenised.

EXAMPLE 5

A fabric of polyethylene glycol terephthalate filaments, bleached in the usual manner, is impregnated with a solution of 1 g/l of the compound of Example 1a or 1c in perchloroethylene. The textile material treated in this way is squeezed out between rollers until it only retains approx. 100% of its dry weight of perchloroethylene solution, and is then exposed for 30 seconds to a hot air treatment at 200°. The fabric treated in this way shows a marked white effect, which has very good fastness to light and is even more brilliant than the effect which is obtained by otherwise similar treatment with an aqueous dispersion of the particular compound.

EXAMPLE 6

A polyethylene glycol therephthalate fabric bleached in the usual manner is impregnated with an aqueous dispersion which contains 1 g/l of the compound of Example 1b, 1q and 1s. The textile material treated in this way is squeezed out between rollers until it only retains approx. 70% of its dry weight of liquid and is then exposed to a hot air treatment at 190° for 30 seconds.

The fabric treated in this way shows a very good white effect of high fastness to light, wet processing and chlorite.

EXAMPLE 7

6 kg of terephthalic acid dimethyl ester and 5 l of ethylene glycol are mixed with 0.05% of zinc acetate and 0.03% (relative to terephthalic acid dimethyl ester) of one of the compounds listed in Example 1u to 1z, in a stirred autoclave. The autoclave is heated to 180° whilst stirring and the methanol eliminated is distilled off. After 1 hour, the temperature is raised to 200°C and after a further 45 minutes it is raised to 220°C. After a total of 2¾ hours, the trans-esterification is complete and the product thus obtained is forced under nitrogen into an autoclave, heated to 275°C, to undergo pre-condensation. Excess glycol is distilled off through a condenser. After 45 minutes, a slight vacuum is first applied, and this is increased to (less than) 1 mm Hg over the course of a further 45 minutes. The polycondensation is complete after 2½ hours. The resulting product is then spun in a known manner to give filaments. The filaments thus produced show a strong, clear brightening of very good fastness to light and to wet processing.

We claim:

1. Compounds of the formula:

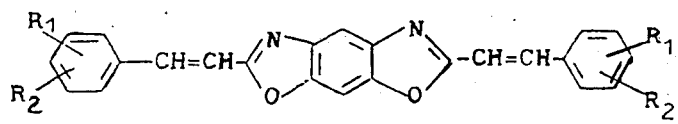

wherein $R_1$ and $R_4$ independently of one another are hydrogen; halogen; nitrile; alkyl containing 1-6 C atoms which is unsubstituted or substituted with OH, $C_1$–$C_4$ alkylcarbonyloxy, F, Cl, or Br; alkoxy containing 1-6 C atoms which is unsubstituted or substituted with OH, $C_1$–$C_4$ alkylcarbonyloxy, F, Cl, or Br; cycloalkyl having 5-7 ring members which is unsubstituted or substituted with $C_1$–$C_4$ alkyl; phenyl; phenyl substituted with 1 to 3 $C_1$–$C_4$ alkyl groups; $C_1$–$C_4$ alkoxycarbonyl unsubstituted or substituted with OH, F, Cl, Br, or $C_1$–$C_4$ alkoxy; or carboxyl.

2. Compounds according to claim 1, wherein $R_1$ denotes hydrogen, $C_1$–$C_4$-alkyl, $C_1$–$C_4$-alkoxy, $C_1$–$C_2$-alkoxy-$C_1$–$C_4$-alkoxy, chlorine, nitrile, phenyl, carboxyl or $C_1$–$C_4$-alkoxycarbonyl and $R_2$ denotes hydrogen, $C_1$–$C_4$-alkyl or chlorine.

3. Compounds according to claim 1, wherein $R_1$ represents hydrogen or m-located $C_1$–$C_4$-alkyl, $C_1$–$C_4$-alkoxy or chlorine and $R_2$ denotes hydrogen.

4. The compound of the formula

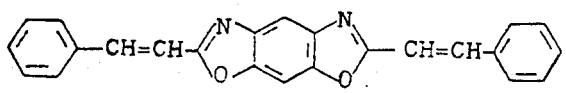

5. The compound of the formula

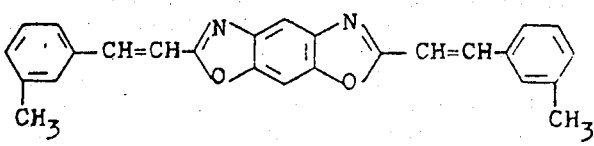

* * * * *